United States Patent [19]

Neurath

[11] Patent Number: 5,039,522
[45] Date of Patent: Aug. 13, 1991

[54] IMMUNOGENS CONTAINING PEPTIDES WITH AN ATTACHED HYDROPHOBIC TAIL FOR ADSORPTION TO HEPATITIS B VIRUS SURFACE ANTIGEN

[75] Inventor: Alexander R. Neurath, New York, N.Y.

[73] Assignee: New York Blood Center, Inc., New York, N.Y.

[21] Appl. No.: 149,789

[22] Filed: Jan. 29, 1988

[51] Int. Cl.[5] .................. A61K 39/29; A61K 39/295; C07K 17/02
[52] U.S. Cl. .................................... 424/89; 530/404; 530/405; 530/406
[58] Field of Search .................. 424/88, 89; 514/2, 8, 514/23, 54; 530/395, 404, 405, 406, 411, 806, 812, 390, 391, 371, 345

[56] References Cited

U.S. PATENT DOCUMENTS

| 3,976,767 | 8/1976 | Neurath | 424/89 |
| 4,578,269 | 3/1986 | Morein | 424/88 |
| 4,818,527 | 4/1989 | Thornton et al. | 424/88 |

FOREIGN PATENT DOCUMENTS

| 0244719 | 11/1987 | European Pat. Off. | 530/395 |
| 0294071 | 12/1988 | European Pat. Off. | |

OTHER PUBLICATIONS

Hepatitis B Virus Surface Antigen (HBsAG) as Carrier for Synthetic Peptides Having an Attached Hydrophobic Tail, Molecular Immunology, vol. 26, No. 1, 1989, pp. 53–62; A. R. Neurath et al.
Journal of Experimental Medicine, vol. 167, Feb. 1988, pp. 658–663; G. H. Lowell et al.; Peptides Bound to Proteosomes Via Hydrophobic Feet Become Highly Immunogenic Without Adjuvants.
Molecular Immunology, vol. 24, 1987, pp. 523–529; A. Machida et al.; A Synthetic Peptide Coded for by the PRE-S2 Region of Hepatitis B Virus for Adding Immunogenicity to Small Spherical Particles Made of the Product Of The S gene.
J. Gen. Virology, vol. 28, 1975, pp. 251–254, A. R. Neurath et al.; Hydrohobic Chromatography of Hepatitis B Surface Antigen on 1,9-Diaminononane or 1,10-Diaminodecane Linked to Agarose.
A. R. Neurath, S. B. H. Kent, "The PreS Region of Hepadnavirus Envelope Proteins", in K. Maramorosh, F. A. Murphy, A. J. Shatkin, eds., *Advances in Virus Research*, vol. 32, Orlando, Fla., Academic Press, (1987).
A. R. Neurath, S. B. H. Kent in *Immunochemistry of Viruses*, "The Basis of Sero-Diagnosis and Vaccines", pp. 324–357, eds. M. H. V. Van Regenmortel and A. R. Neurath, Elsevier, Amsterdam, (1985).
Lowell et al. (1988), J. Expt'l Med., 167:658–663.
Neurath et al., (1989), Mol. Immunol., 26:53–62.
Sanchez et al., (1983), J. Med. Virol., 11:115–124.

Primary Examiner—Margaret Moskowitz
Assistant Examiner—Kay Kim
Attorney, Agent, or Firm—Sprung, Horn, Kramer & Woods

[57] ABSTRACT

An immunogenic complex comprising a peptide containing a hydrophobic tail, the peptide being adsorbed to hepatitis B virus surface antigen via the hydrophobic tail. Such complex in a immunogenically effective amount when administered with a physiologically acceptable diluent and an adjuvant can serve as a vaccine.

17 Claims, 5 Drawing Sheets

IMMUNOGENS CONTAINING PEPTIDES WITH AN ATTACHED HYDROPHOBIC TAIL FOR ADSORPTION TO HEPATITIS B VIRUS SURFACE ANTIGEN

This invention was made with United States government support under Grant CA 43315 from the NIH. The United States government has certain rights in this invention.

BACKGROUND OF THE INVENTION

1. Field of the Invention

The present invention concerns improved immunogens containing peptides. More particularly, the invention relates to peptides with an attached hydrophobic tail for adsorption to hepatitis B surface antigen.

2. Background Information

Peptides corresponding to surface regions of different viruses or of other infectious agents may represent potential immunogens with application for vaccination against the respective infectious diseases. However, such peptides frequently require a combination of carriers and adjuvants to become sufficiently immunogenic for consideration as vaccines.

In the case of hepatitis B virus (HBV), the preS1 and preS2 region of the hepatitis B virus envelope protein elicits virus-neutralizing protective antibodies. However, these regions of the hepatitis B virus envelope protein are usually underrepresented in preparations of hepatitis B virus surface antigen (HBsAg) obtained from plasma or from other sources based on recombinant DNA technology. This underrepresentation of preS2 and especially of preS1 sequences is due to a blockade of secretion from eukaryotic cells of HBsAg containing these sequences. Therefore, a combination of synthetic peptides derived from the preS2 and especially from the preS1 sequence with HgsAg particles, consisting predominantly of the S-protein sequence is expected to result in an improved immunogen eliciting protective virus neutralizing antibodies of the broadest possible specificity (A. R. Neurath, S. B. H. Kent, "The PreS Region of Hepadnavirus Envelope Proteins", in K. Maramorosh, F. A. Murphy, A. J. Shatkin, eds., *Advances in Virus Research*, Vol. 32, Orlando, Fla., Academic Press, (1987)).

The addition to hepatitis B virus surface antigen of polypeptide sequences expected to elicit protective antibodies against hepatitis B (or against other unrelated infectious agents) can theoretically be accomplished by chemically linking synthetic peptides to HBsAg. Such linkage requires chemically active groups on both the peptide and on the surface of HBsAg (for example, SH groups, epsilon-amino groups of lysines, or N-terminal amino groups). HBsAg does not have available free SH groups, since the cysteine residues of HBsAg are all involved in the formation of disulfide bonds within the HBsAg protein. These bonds are absolutely necessary for the antigenicity and immunogenicity of HBsAg particles. The epsilon-amino groups on the surface of HBsAg play important roles in the immunogenicity and antigenicity of HBsAg as well (reviewed by A. R. Neurath and S. B. H. Kent in *Immunochemistry of Viruses*, "The Basis of Sero-Diagnosis and Vaccines", pp. 324-357, eds. M. H. V. Van Regenmortel and A. R. Neurath, Elsevier, Amsterdam, (1985)). For this reason, the chemical linkage of sufficient quantities of synthetic peptides to HBsAg particles cannot be accomplished without resulting in a deleterious effect on the antigenicity and immunogenicity of S-protein. For this reason, there has been a great need to find methods which would allow the attachment of synthetic peptides to HBsAg, not involving a chemical linkage, but strong enough to allow the HBsAg protein to function as a carrier for the synthetic peptide and for the only approved adjuvant alum to function as an adjuvant for HBsAg and the synthetic peptides of choice HBsAg has on its surface exposed hydrophobic regions which interact strongly with hydrophobic (long aminoalkyl, alkyl or aromatic chains) residues exposed on the surface of various adsorbents Such hydrophobic interaction is the basis of the method to purify HBsAg from serum and from other biological fluids (U.S. Pat. No. 3,976,767, issued Aug. 24, 1976).

| DEFINITIONS | | |
|---|---|---|
| Amino Acid Code Words | | |
| D | Asp | aspartic acid |
| N | Asn | asparagine |
| T | Thr | threonine |
| S | Ser | serine |
| E | Glu | glutamic acid |
| Q | Gln | glutamine |
| P | Pro | proline |
| G | Gly | glycine |
| A | Ala | alanine |
| C | Cys | cysteine |
| V | Val | valine |
| M | Met | methionine |
| I | Ile | isoleucine |
| L | Leu | leucine |
| Y | Tyr | tyrosine |
| F | Phe | phenylalanine |
| W | Trp | tryptophane |
| K | Lys | lysine |
| H | His | histidine |
| R | Arg | arginine |
| HBV | | hepatitis B virus |
| HBsAg | | hepatitis B surface antigen |
| DNA | | deoxyribonucleic acid |

SUMMARY OF THE INVENTION

The present invention is directed to an immunogenic complex containing a peptide, e.g., a synthetic peptide, containing a hydrophobic tail, the peptide being adsorbed to hepatitis B surface antigen via the hydrophobic tail. The invention also relates to a vaccine comprising an immunologically effective amount of the aforementioned complex, a physiologically acceptable diluent and an adjuvant.

DETAILED DESCRIPTION OF THE INVENTION

It is possible to add any peptide with a hydrophobic tail to HBsAg particles. The HBsAg particles consisting either of S-protein only or of S-protein and preS2 sequences derived, e.g., either from serum of HBV carriers or through recombinant DNA techniques. Thus, it is possible using the present invention to prepare immunogens based on a combination of peptides, preferably synthetic peptides, and of HBsAg. The peptide can correspond to amino acid sequences from hepatitis B virus specific proteins, or from proteins of other infectious agents, e.g., HIV, resulting in multivalent vaccines containing immunogens specific for both hepatitis B virus and for any other selected infectious agent.

Generally, the peptide for use in the invention will have at least 5 amino acids and will have no more than 100 amino acids, preferably no more than 75 amino acids and more preferably no more than 50 amino acids.

Preferred peptides for use in the present invention are hepatitis B virus peptides of the preS regions, either of the preS1 or preS2 regions. However, peptides of other pathogens, e.g., human immunodeficiency virus (HIV), can be used. Such peptides preferably have an amino acid sequence which corresponds to, i.e., mimics, an amino acid sequence of a pathogen The hepatitis B virus (HBV) has two DNA strands, namely the long (L) strand and the short (S) strand. The L strand transcript has four open reading frame regions which are termed (S+preS), C, P and X.

The open reading frame region (S+preS) corresponds to the envelope (env) gene of HBV DNA and codes for a family of proteins found in the HBV envelope and in virus related particles A schematic representation of the potential translation products of the env gene(s) of HBV DNA is as follows:

The numbers in the above schematic refers to amino acids (AA). A translation initiation site at Met 1 exists for the adw$_2$ and adr subtypes only. The first amino acid for the other subtypes correspond to position preS 12.

Hereinafter, amino acid sequences corresponding to the preS region (env 1 to 174) are designated with the prefix "preS" and amino acid sequences corresponding to the S region (env 175 to 400) are designated by the prefix "S". In the env gene product representation, the S region spans amino acids 175 to 400, as compared to amino acids 1 to 226 in the "S region only" representation.

In the above schematic, the preS region is defined by amino acid sequence positions preS 1 to amino acid sequence position pre-S 174. The S region is defined by sequence positions S 1 (amino acid 175 of the open reading frame and adjacent to pre-S 174) to sequence position S 266 (amino acid 400 of the open reading frame). The S-gene product (S-protein) consists of this amino acid sequence.

The naturally occurring envelope proteins of hepatitis B virus include the following:

(1) a full length translational product of the env gene oil-HBV, i.e., for adw$_2$ and adr preS(1-174)+S(1-75-400)=400 amino acids, for ayw, adyw and adw preS(12-174)+S(1-226)=389 amino acids (env 12-400);

(2) preS(120-174)+S(175-400)=281 amino acids (env 120-400)=terminal 55 amino acids in the preS region+226 amino acids comprising the entire S region (the corresponding proteins approximately 33 and 36 kD in size (GP33 and GP36), and differing from each other in the extent of glycosylation); and (3) S(1-226)=226 amino acids, i.e., the entire S region (env 175-400); representing the approximately 22 and 26 kD major constituents of the HBV envelope (P22 and P26) in their non-glycosylated and glycosylated forms (the "S-protein").

Preferred preS peptides for use in the present invention include the following:

(1) preS(12–32), all subtypes,
(2) preS(120–145), all subtypes,
(3) preS(32–53), all subtypes,
(4) preS(117–134), all subtypes,
(5) preS(94–117), all subtypes,
(6) preS(153–171), all subtypes,
(7) preS(1–21), all subtypes,
(8) preS(57–73), all subtypes,
(9) preS(1–12), subtype adw$_2$,
(10) preS(1–12), subtype adr,
(11) preS(12–47), all subtypes,
(12) preS(21–47), all subtypes,
(13) preS(120–153), all subtypes,
(14) preS(132–137), all subtypes,
(15) preS(53–73), all subtypes,
(16) preS(128–139), all subtypes,
(17) preS(15–47), all subtypes.

Furthermore peptide analogs of the following non-limiting examples of viruses can be employed in the present invention: influenza hemagglutinin (A/memphis/102/72 strain, A/Eng 1878/69 strain, A/NT/60/68/29c strain, and A/Qu/7/70 strain), fowl plague virus hemagglutinin, vaccinia, polio, rubella, cytomegalovirus, small pox, herpes simplex types I and II, yellow fever, infectious ectromelia virus, Cowpox virus, infectious bovine rhinotracheitis virus, equine rhino-pneumonitis (equine abortion) virus, malignant catarrh virus of cattle, feline rhinotracheitis virus, canine herpes virus, Epstein-Barr virus (associated with infectious mononucleosis and Burkitt lymphoma), Marek's disease virus, sheep pulmonary adenomatosis (Jaagziekte) virus, cytomegaloviruses, adenovirus group, human papilloma virus, feline panleucopaenia virus, mink enteritis virus, African horse sickness virus (9 serotypes), blue tongue virus (12 serotypes), infectious pancreatic necrosis virus of trout, fowl sarcoma virus (various strains), avian leukosis virus (visceral, erythroblastic and myeloblastic), osteopetrosis virus, Newcastle disease virus, parainfluenza virus 1, parainfluenza virus 2, parainfluenza virus 3, parainfluenza 4, mumps virus, turkey virus, CANADA/58, canine distemper virus, measles virus, respiratory syncytial virus, myxovirus, Type A viruses such as human influenza viruses, e.g., Ao/PR8/34, A1/CAM/46, and A2/Singapore/1/57, fowl plague virus, Type B influenza viruses, e.g., B/Lee/40, rabies virus, eastern equinine encephalitis virus, Venezuelan equine encephalitis virus, western equine encephalitis virus, yellow fever virus, Dengue type 1 virus (=type 6), Dengue type 2 virus (=type 5), Dengue type 3 virus, Dengue type 4 virus, Japanese encephalitis virus, Kyasanur Forest virus, Louping ill virus, Murray Valley encephalitis virus, Omsk hemorrhagic fever virus (types I and II), St. Louis encephalitis virus, human rhinoviruses, foot-and-mouth disease virus, poliovirus type 1, enterovirus polio 2, enterovirus polio 3, avian infectious bronchitis virus, human respiratory virus, transmissible gastroenteritis virus of swine, lymphocytic choriomeningitis virus, lassa virus, Machupo virus, Pichinde virus, Tacaribe virus, Papillomavirus, simian virus and Sindbis virus, and the like.

Peptide analogs of bacteria, for example, leprosy, tuberculosis, syphilis and gonorrhea, can also be used in the present invention.

Peptide analogs of the following parasites: organisms carrying malaria (P. Falciparum, P. Ovace, etc.), Schistosomiasis, Onchocerca Volvulus and other filiarial parasites, Trypanosomes, Leishmania, Chagas disease, amoebiasis, hookworm, and the like can also be utilized in the present invention.

The following peptides are non-limiting examples of peptides that can be utilized in the present invention:

A peptide containing an amino acid sequence mimicking the antigenic determinant of polyoma virus medium size tumor antigen is Lys-Arg-Ser-Ars-His-Phe (G. Walter, M. A. Hutchinson, T. Hunter and W. Eckhart, "Purification of Polyoma Virus Medium-Size Tumor Antigen by Immunoaffinity Chromatography", *Proc. Natl. Acad. Sci U.S.A.*, 79, 4025–4029, (1982)).

Peptides containing an amino acid sequence mimicking the antigenic determinant of simian virus 40 large tumor antigen are as follows:
Met-Asp-Lys-Val-Leu-Asn-Arg and
Lys-Pro-Pro-Thr-Pro-Pro-Pro-Glu-Pro-Glu-Thr
(G. Walter, K. H. Scheidtmann, A. Carbone, A. P. Laudano, R. A. Lerner, N. Green, H. Alexander, F.-T. Liu, J. G. Sutcliffe and T. M. Shinnick, "Chemically Synthesized Peptides Predicted From the Nucleotide Sequence of the Hepatitis B Virus Genome Elicit Antibodies Reactive With the Native Envelope Protein of Dane Particles", *Proc. Natl. Acad. Sci. U.S.A.*, 78, 6, 3403–3407, (1981)).

A peptide containing an amino acid sequence mimicking the antigenic determinant of retrovirus R antigen is as follows:
Leu-Thr-Gln-Gln-Phe-His-Gln-Leu-Lys-Pro
Ile-Glu-Cys-Glu-Pro
(J. G. Sutcliffe, T. M. Shinnick, N. Green, F.-T. Liu, H. L. Niman and R. A. Lerner, "Chemical Synthesis of A Polypeptide Predicted From Nucleotide Sequence Allows Detection Of A New Retroviral Gene Product", *Nature*, 287, (1980)).

A peptide containing an amino acid sequence mimicking the antigenic determinant of avian sarcoma virus antigen is as follows:
Glu-Asp-Asn-Glu-Tyr-Thr-Ala-Arg-Gln-Gly,
(T. W. Wong and Alan R. Goldberg, "Synthetic Peptide Fragment Of src Gene Product Inhibits the src Protein Kinase and Cross Reacts Immunologically With Avian onc Kinases and Cellular Phosphoproteins", *Proc. Natl. Acad. U.S.A.*, 78, 12, 7412–7416, (1981)).

Peptides containing an amino acid sequence mimicking the antigenic determinant of foot-and-mouth disease virus antigen are as follows:

141
Val Pro Asn Leu Arg Gly Asp Leu Gly Val

160
Leu Ala Gly Lys Val Ala Arg Thr Leu Pro and

201
His Lys Gln Lys Ile Val Ala Pro Val Lys Gln Thr Leu, (J. L. Bittle, R. A. Houghten, H. Alexander, T. M. Shinnick, J. G. Sutcliffe, R. A. Lerner, D. J. Rowlands and F. Brown, "Protection Against Foot-And-Mouth Disease By Immunization With A Chemically Synthesized Peptide Predicted From the Viral Nucleotide Sequence", *Nature*, 298, 30–33, (1982)).

A peptide containing an amino acid sequence the antigenic determinant of hemagglutinin X-31 (H3N2) influenza virus antigen is as follows:

```
        123       125
        Glu—Gly—Phe—Thr—Trp—Thr—Gly—

130                   135
        Val—Thr—Gln—Asn—Gly—Gly—Ser—

140
        Asp—Ala—Cys—Lys—Arg—Gly—Pro—

145                  150  151
        Gly—Ser—Gly—Phe—Phe—Ser—Arg—Leu
```

(D. C. Jackson, J. M. Murray, D. O. White, C. N. Fagan and G. W. Tregear, "Antigenic Activity of a Synthetic Peptide Comprising the 'Loop' Region of Influenza Virus Hemagglutinin", *Virology*, 120, 273–276, (1982)).

A peptide containing an amino acid sequence mimicking the antigenic determinant of hemagglutinin of type A H3N2 influenza virus antigen was synthesized by G. M. Muller, M. Shapira and R. F. Doolittle, "Antibodies Specific for the Carboxy- And Amino- Terminal Regions of Simian Virus 40 Large Tumor Antigen", *Proc. Natl. Acad. Sci. U.S.A.*, 77, 9, 5179–5200, (1980).

A peptide containing an amino acid sequence mimicking the antigenic determinant of influenza virus strain 3QB antigen is $Ile_1\ Val_1\ Asx_2\ Thr_1\ Ser_2\ Glx_2\ Pro_1\ Gly_3\ Ala_1\ Leu_1\ Lys_1$ (A. Aitken and C. Hannoun, "Purification of Hemagglutinin and Neuraminidase from Influenza Virus Strain 3QB and Isolation of a Peptide From an Antigenic Region of Hemagluttinin", *Eur. J. Biochem.*, 107, 51–56, (1980)).

Peptides containing an amino acid sequence mimicking the antigenic determinant of diphtheria antigen are as follows:

```
                    Natural DT Loop

—Cys—Ala—Gly—Asn—Arg—Val—Arg—Arg—Ser—Val—
           186              190                 195

Gly—Ser—Ser—Leu—Lys—Cys—
                                      201

Synthetic Peptide

Tetradecapeptide          Gly(188)—Cys-(201)
        Hexadecapeptide           Cys(186)—Cys-(201)
        Octadecapeptide       Ala—Ala—Cys(186)—Cys-(201)
```

(F. Audibert, M. Jolivet, L. Chedid, R. Arnon and M. Sela, "Successful Immunization With a Totally Synthetic Diphtheria Vaccine", *Proc. Natl. Acad. Sci. U.S.A.*, 79, 5042–5046, (1982).

A peptide containing an amino acid sequence mimicking the antigenic determinant of Streptococcus pyogenes M antigen is as follows:

```
                 5
        Asn—Phe—Ser—Thr—Ala—Asp—Ser—Ala—Lys 10              15
        Ile—Lys—Thr—Leu—Glu—Ala—Glu—Lys—Ala—Ala—

20          25
        Leu—Ala—Ala—Arg—Lys—Ala—Asp—Leu—Glu—Lys—

30              35
        Ala—Leu—Glu—Gly—Ala—Met
```

(E. H. Beachey, J. M. Seyer, D. B. Dale, W. A. Simpson and A. H. Kang, "Type-Specific Protective Immunity Evoked by Synthetic Peptide of Streptococcus Pyogenes M Protein", *Nature*, 292, 457–459, (1981)).

The chemical synthesis of peptides (to produce "synthetic peptides") is described in the following publications: S. B. H. Kent, *Biomedical Polymers*, eds. Goldberg, E. P. and Nakajima, A. (Academic Press, New York), 213–242,(1980); A. R. Mitchell, S. B. H. Kent, M. Engelhard, and R. B. Merrifield, *J. Org. Chem.*, 43, 2845–2852, (1978); J. P. Tam, T.-W. Wong, M. Riemen, F.-S. Tjoeng, and R. B. Merrifield, *Tet. Letters*, 4033–4036, (1979); S. Mojsov, A. R. Mitchell, and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.), in press, 1981.

*Chemical Synthesis:* In the so-called "Merrifield solid phase procedure" the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;
(b) neutralized by mixing for 10 minutes at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysin) or other protecting groups commonly used in peptide synthesis.
(e) the activated amino acid is reacted with the peptide-resin for two hours at room temperature, resulting in addition of the new amino acid to the end of the growing peptide chain.
(f) the peptide-resin is washed with methylene chloride;
(g) the N-alpha-(tert. butyloxycarbonyl) group is removed from the most recently added amino acid by reacting it with 30 to 65%, preferably 50% (v/v) trifluoroacetic acid in methylene chloride for 10 to 30 minutes at room temperature;
(h) the peptide-resin is washed with methylene chloride; and
(i) steps (a) through (h) are repeated until the required peptide sequence has been constructed.

The peptide is then removed from the resin and simultaneously the side-chain protecting groups are removed by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Isolation from natural sources: If sufficient quantities of the whole protein antigen are available, a limited portion of the molecule, bearing the desired sequence of amino acids may be excised by any of the following procedures:

(a) Digestion of the protein by proteolytic enzymes, especially those enzymes whose substrate specificity results in cleavage of the protein at sites immediately adjacent to the desired sequence of amino acids;

(b) Cleavage of the protein by chemical means. Particular bonds between amino acids can be cleaved by reaction with specific reagents. Examples include: bonds involving methionine are cleaved by cyanogen bromide; asparaginyl-glycine bonds are cleaved by hydroxylamine;

(c) A combination of proteolytic and chemical cleavages.

It should also be possible to clone a small portion of the DNA, either from natural sources or prepared by synthetic procedures, or by methods involving a combination thereof, that codes for the desired sequence of amino acids, resulting in the production of the peptide by bacteria, or other cells.

Hydrophobic tails can be covalently linked to peptides of the present invention by reacting a peptide containing one or more cysteine residues, preferably a peptide containing such cysteine residue at a N- or C-terminus of the peptide, with a long chain, aliphatic mercaptan of the formula $C_nH_{2n+1}SH$ or $C_nH_{n+2}COSH$, wherein n is an integer from 7 to 30 and preferably from 9 to 18. Alternatively, a hydrophobic tail can be chemically added to a synthetic peptide by reacting an alpha-amino group of the peptide with a long chain aldehyde having 7 to 30 carbon atoms, preferably 9 to 18 carbon atoms or with an acid anhydride. Non-limiting examples of such long chain aldehydes include the following: myristyl aldehyde, lauraldehyde and decyl aldehyde. Non-limiting examples of acid anhydrides for use in the present invention include the following: lauric acid anhydride, myristic acid anhydride, stearic acid anhydride and palmitic acid anhydride.

The immunogen of the present invention can be employed with a physiologically acceptable diluent (medium), e.g., phosphate buffered saline and an adjuvant, e.g., alum, in order to provide a vaccine. Generally speaking, the synthetic peptide concentration in a physiologically acceptable medium will be between approximately less than 1 milligram and more than 10 micrograms per dose.

The vaccine can be administered by subcutaneous, intradermal or intramuscular injection. While the preferred route would depend upon the particular vaccine, it is believed that intramuscular injection will be generally suitable. Generally speaking, the vaccine will be administered in two doses about one month apart followed by a booster at six months to one year after primary immunization. The subsequent doses or the booster will depend on the level of antibody in the blood as a result of the initial immunization and in certain instances may be unnecessary.

The invention will now be described with reference to the following non-limiting examples.

Examples

Example 1: Myristilation of Peptide PreS(12-47) with C-Terminal Gly-Gly-Cys (GGC)

Figure 1:
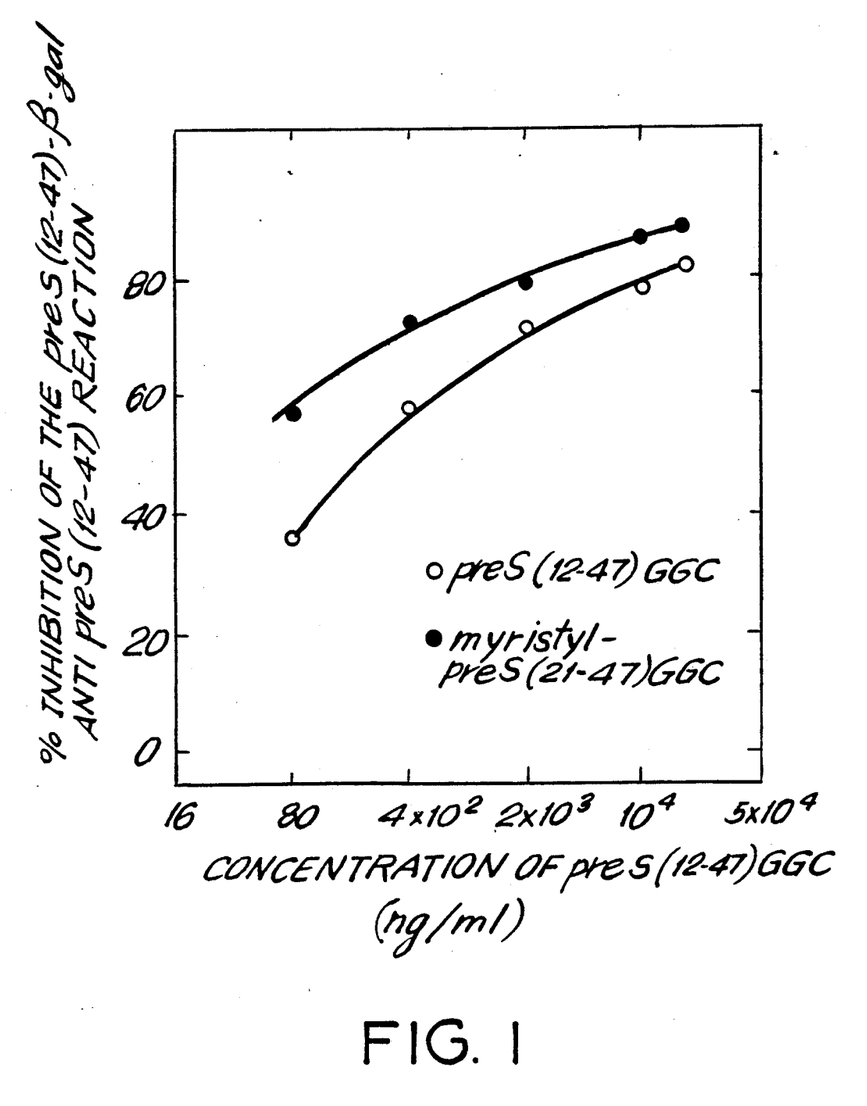
FIG. 1 is a graph depicting the inhibition of the reaction between hepatitis preS(21-47)-betagalactosidase and anti-preS(21-47) by the free preS(21-47) peptide (o) and by myristilated preS(12-47) (●).

Two milligrams of the peptide preS(12-47)-GGC were dissolved in absolute ethanol adjusted to pH 9 and twenty milligrams of myristic acid anhydride in ethanol were added. The mixture was maintained six hours at 20° C. The pH was maintained at 9. Then, one milligrax of pyridyldisulfide was added (to enhance the formation of peptide dimers expected to be more immunogenic). The mixture was maintained at 20° for another 30 minutes and then dialyzed consecutively, first, against a mixture of distilled water and ethanol; then against distilled water; and finally against phosphate buffered saline (PBS). The resultant product was tested for antigenicity (ability to react with antibodies to the synthetic peptide) in a competition test measuring the competition between free peptide and the myristilated peptide, respectively, in the reaction of a peptide beta-galactosidase conjugate with anti-peptide antibodies. Surprisingly, the myristilated peptide reacted with antibodies preferably as compared to free non-myristilated peptide. See FIG. 1.

Example 2: Preparation of the Complex, Myristilated PreS(12-47)-HBsAg

Two milligrams (based on the weight of the synthetic peptide before myristilation) of myristilated preS(12-47) were mixed with two milligrams of HBsAg particles, synthesized in CHO cells and containing preS2 sequences (M. Michel, P. Pontisso, E. Sobczak, Y. Malpiece, R. E. Streek and P. Tiollais, (1984), "Synthesis In Animal Cells of Hepatitis B Surface Antigen Particles Carrying a Receptor for Polymerized Human Serum Albumin", *Proc. Nat. Acad. Sci. U.S.A.*, 81, 7708-7712). After incubation at 20° C. for at least one hour, the complex was characterized by several analyses and used as an immunogen.

Figure 2:
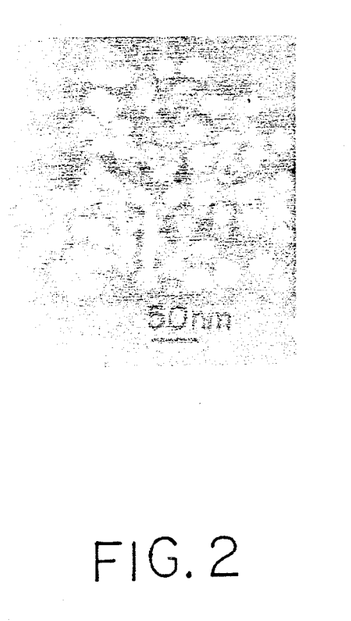
FIG. 2 is a photograph of an electron micrograph of an immune precipitate generated by reacting HBsAg particles complexed with myristilated preS(12-47) with anti-preS(12-47).
Figure 3:
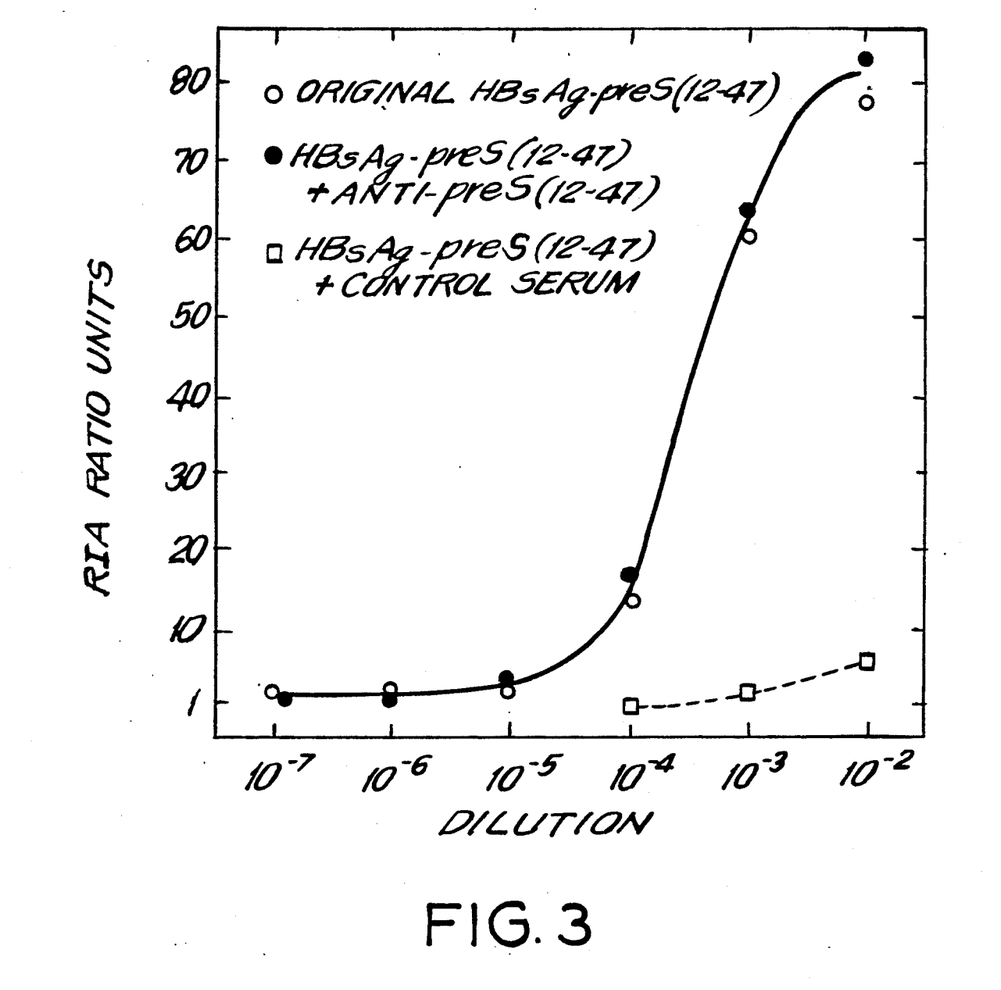
FIG. 3 is a graph which indicates that anti-preS(-12-47) quantitatively precipitates all HBsAg S-protein present in complexes generated by adding myristilated preS(12-47) to HBsAg-CHO particles.
Figure 4:
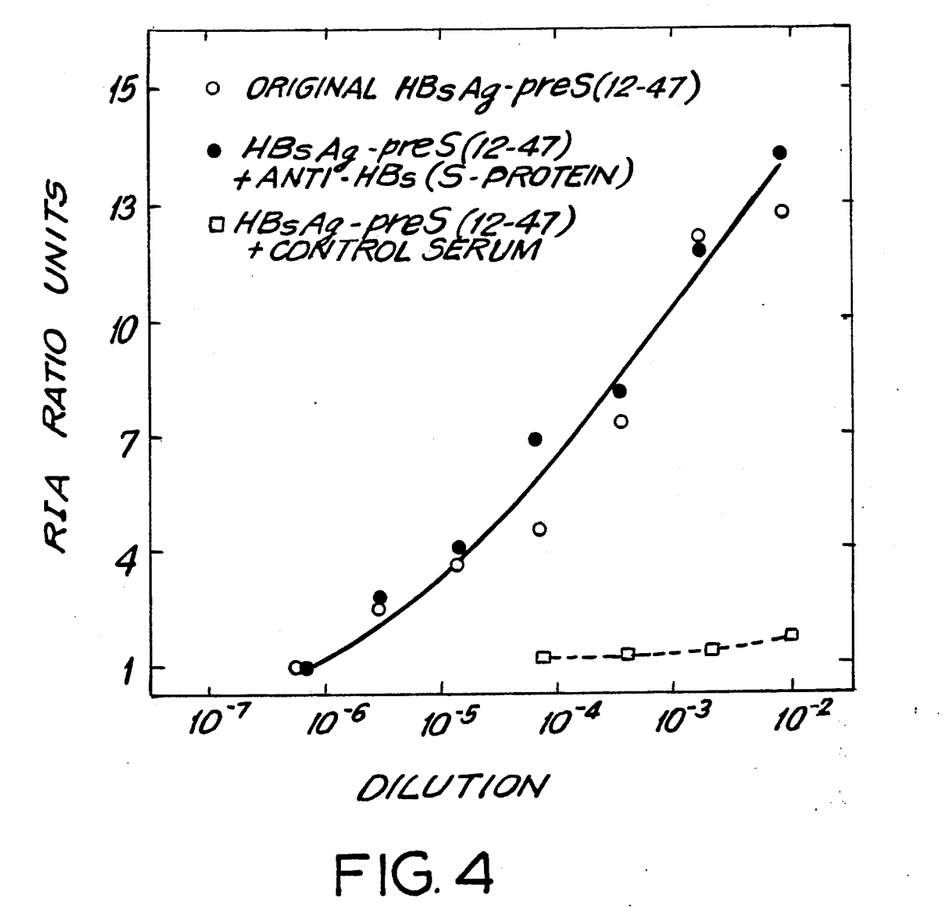
FIG. 4 is a graph which indicates that anti-HBs (S-protein) quantitatively precipitates myristilated preS(-21-47) added to HBsAg-CHO particles.

To prove that the preS(12-47) peptide was indeed attached to HBsAg particles, the complex (corresponding to 50 ug of HBsAg-CHO particles) was reacted with one milligram of IgG isolated from a hyperimmune serum against the synthetic peptide preS(12-47)adw$_2$ or with the control normal rabbit serum. The respective mixtures were maintained for 30 to 60 minutes at 37° C. and at 4° C. for at least 16 hours. A visible precipitate formed in the mixture containing the antipeptide antibody, but no precipitate formed when normal rabbit IgG was added instead of the antibody. Immune complexes could be visualized by electron microscopy in the mixture of preS(12-47)-HBsAg to which antipeptide antibodies were added. See FIG. 2. The precipitate was centrifuged, dissolved in 3M NaSCN, serially diluted in 3M NaSCN; and the serial dilutions were used to coat polystyrene beads. HBsAg attached to the beads was detected by $^{125}$I-labeled antibodies to the HBsAg S-protein. The results obtained (FIG. 3) show that all HBsAg initially present before adding antipeptide antibodies was indeed completely precipitated by the antipeptide antibodies, clearly indicating that all HBsAg became complexed with the synthetic peptide preS(-12–47). In a reverse experiment, reaction with anti-HBs resulted in quantitative precipitation of preS(12–47) proving that 100% of the myristilated peptide was adsorbed to CHO-HBsAg (FIG. 4).

Example 3: Testing for Immunogenicity

Five doses of each of the following immunogens, 200 μg each, were administered in bi-weekly doses to rabbits:

(1) preS(12–47) administered with complete Freund's adjuvant, (2) myristilated preS(12–47) administered with incomplete Freund's adjuvant, (3) HBsAg-CHO particles with covalently linked preS(12–47) (preS(12–47)-SDPP-CHO-HBsAg), administered with complete Freund's adjuvant, (4) complex formed by the adsorption of myristilated preS(12–47) to HBsAg-CHO particles, administered with complete Freund's adjuvant.

In each case where complete Freund's adjuvant was used for the first immunization, all subsequent immunization were conducted with incomplete Freund's adjuvant. Two rabbits were used per immunogen; geometric mean antibody titers are plotted.

Figure 5:
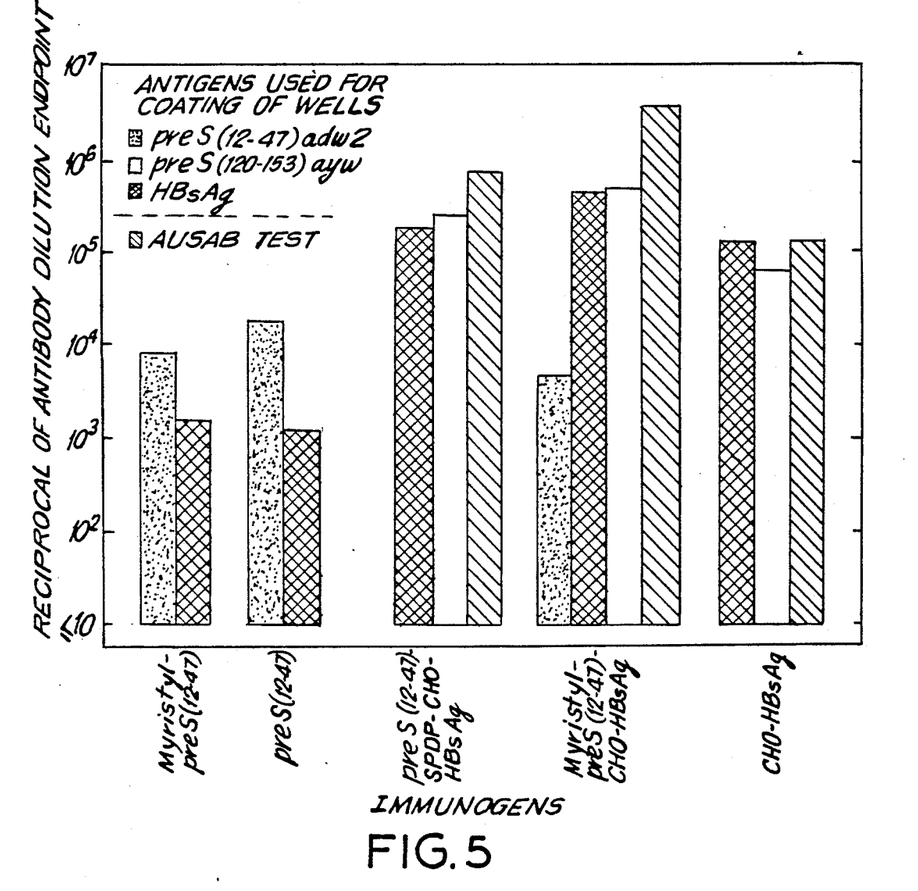
FIG. 5 is a series of bar graphs depicting the comparative immunogenicity of preS(12-47) administered with complete Freund's adjuvant; of myristilated preS(-12-47) administered with incomplete Freund's adjuvant; of HBsAg-CHO particles with covalently linked preS(12-47) (preS(12-47)-SPDP-CHO-HBsAg) and of complexes formed by the adsorption of myristilated preS(12-47) to HBsAg-CHO particles (the latter two preparations were administered with complete Freund's adjuvant).

The complex of myristilated preS(12–47) with HBsAg particles elicited high levels of antibodies against preS1 and preS2 sequences of the HBV envelope protein and against S-protein as shown in FIG. 5. On the other hand, covalent linking of preS(-12–47)GGC to CHO-HBsAg particles (50 μg peptide per mg HBsAg) resulted in an immunogen which failed to elicit anti-preS1-specific antibodies. The addition of preS(12–47) sequences to the recombinant particles did not result in a diminished immune response to preS2 sequences and to S-protein. Therefore, the complex myristilated preS(12–47)CHO-HBsAg represents a preferably immunogen for vaccination against hepatitis B, since it elicits antibodies with all possible (preS1, preS2 and S-protein) specificities involved in virus neutralization and protection.

Unexpectedly, the attachment of myristyl-preS(-12–47) to HBsAg particles resulted in an enhanced response to the S-protein as measured by the AUSAB test (see FIG. 5). Thus, the addition of preS1-specific peptides to HBsAg particles is expected to result in hepatitis B vaccines with significantly enhanced immunogenicity.

It will be appreciated that the instant specification and claims are set forth by way of illustration and not limitation and that various modifications and changes may be made without departing from the spirit and scope of the present invention.

What is claimed is:

1. An immunogenic complex comprising a peptide to which has been attached a hydrophobic tail, said peptide being adsorbed to particles comprising intact hepatitis B virus surface antigen via said hydrophobic tail.

2. An immunogenic complex according to claim 1, wherein the peptide is a hepatitis B virus preS peptide.

3. An immunogenic complex according to claim 1, wherein the hydrophobic tail is covalently linked to the peptide by reacting the peptide containing one or more cysteine residues with a long chain, aliphatic mercaptan of the formula $C_nH_{2n+1}SH$ or $C_nH_{2n+2}COSH$, wherein n is an integer from 7 to 30.

4. An immunogenic complex according to claim 3, wherein the cysteine residues are disposed at the N- or C-terminus of the peptide.

5. An immunogenic according to claim 3, wherein n is 9 to 18.

6. An immunogenic complex according to claim 1, wherein the hydrophobic tail is covalently linked to the peptide by reacting an alpha-amino group of the peptide with a long chain aldehyde having 7 to 30 carbon atoms or an acid anhydride having 7 to 30 carbon atoms.

7. An immunogenic complex according to claim 6, wherein the aldehyde has 9 to 18 carbon atoms.

8. An immunogenic complex according to claim 6, wherein the acid anhydride has 9 to 18 carbon atoms.

9. An immunogenic complex according to claim 6, wherein the aldehyde is selected from the group consisting of myristyl aldehyde, lauraldehyde and decyl aldehyde.

10. An immunogenic complex according to claim 6, wherein the acid anhydride is selected from the group consisting of lauric acid anhydride, myristic acid anhydride, stearic acid anhydride and palmitic acid anhydride.

11. An immunogenic complex according to claim 1, wherein the peptide is produced by chemical synthesis, cleaved from a natural material or produced by recombinant DNA techniques.

12. An immunogenic complex according to claim 1, wherein the peptide is a synthetic peptide having an amino acid sequence corresponding to an amino acid sequence of the preS region of hepatitis B virus.

13. An immunogenic complex according to claim 1, wherein the peptide is a synthetic peptide having an amino acid sequence corresponding to an amino acid sequence of the preS1 region of hepatitis B virus.

14. An immunogenic complex according to claim 13, wherein the peptide is a synthetic peptide and has an amino acid sequence corresponding to preS(12–47).

15. An immunogenic complex according to claim 1, wherein the peptide has an amino acid sequence corresponding to an amino acid sequence of an antigenic determinant of a pathogen other than hepatitis B virus.

16. An immunogenic complex according to claim 15, wherein the pathogen is HIV.

17. A vaccine comprising an immunologically effective amount of the immunogenic complex according to claim 1, a physiologically acceptable diluent and an adjuvant.

* * * * *